(12) United States Patent
Geltinger et al.

(10) Patent No.: US 9,097,349 B2
(45) Date of Patent: Aug. 4, 2015

(54) SEAL DEVICE WITH COMPENSATION CAPACITY FOR A PLURALITY OF MOVEMENT DIRECTIONS

(71) Applicant: KRONES AG, Neutraubling (DE)

(72) Inventors: Florian Geltinger, Donaustauf (DE); Michael Neubauer, Mintraching (DE)

(73) Assignee: KRONES AG, Neutraubling (DE)

( * ) Notice: Subject to any disclaimer, the term of this patent is extended or adjusted under 35 U.S.C. 154(b) by 11 days.

(21) Appl. No.: 13/955,168

(22) Filed: Jul. 31, 2013

(65) Prior Publication Data

US 2014/0044607 A1 Feb. 13, 2014

(30) Foreign Application Priority Data

Aug. 10, 2012 (DE) .......................... 10 2012 107 361

(51) Int. Cl.
*A61L 9/00* (2006.01)
*F16J 15/44* (2006.01)
*B29C 49/46* (2006.01)
*A61L 2/00* (2006.01)

(52) U.S. Cl.
CPC .. *F16J 15/44* (2013.01); *A61L 2/00* (2013.01); *B29C 49/46* (2013.01); *B29C 2049/4697* (2013.01)

(58) Field of Classification Search
CPC .............. A61L 2/00; A61L 2/22; A61L 9/00; A61L 9/015; A61L 9/03; A61L 9/14
USPC ......................................... 422/1, 28, 305–306
See application file for complete search history.

(56) References Cited

U.S. PATENT DOCUMENTS

| 2005/0079106 A1* | 4/2005 | Baker et al. ................... 422/100 |
| 2011/0287126 A1 | 11/2011 | Geltinger et al. |
| 2012/0070522 A1 | 3/2012 | Voth et al. |

FOREIGN PATENT DOCUMENTS

| DE | 10 2005 006445 | 8/2006 |
| DE | 10 2007 052721 | 5/2009 |
| DE | 10 2011 081414 | 7/2012 |
| EP | 2444232 | 4/2012 |
| FR | 2796903 | 2/2001 |

OTHER PUBLICATIONS

European Search Report from corresponding European Application No. 13179774, dated Oct. 30, 2013.

* cited by examiner

*Primary Examiner* — Monzer R Chorbaji
(74) *Attorney, Agent, or Firm* — Greer, Burns & Crain, Ltd.

(57) ABSTRACT

A seal device is provided for sealing intermediate spaces formed between bodies arranged to be relatively movable, wherein the seal device has a resilient, gas-tight main body which is extendable in a peripheral direction and through which a portion of the first of the two bodies is guided, and a first end portion, which fastenable to the second body, and a second end portion, which is settable against the first movable body, wherein the second end portion is movable with respect to the first end portion in a first transverse direction which extends at an angle different from 0° with respect to a longitudinal direction. A sliding seal device, which is applicable to the first movable body so that a relative rotation is made possible between the first body and the second body by a pre-set angle, is arranged on the second end portion of the seal device.

19 Claims, 3 Drawing Sheets

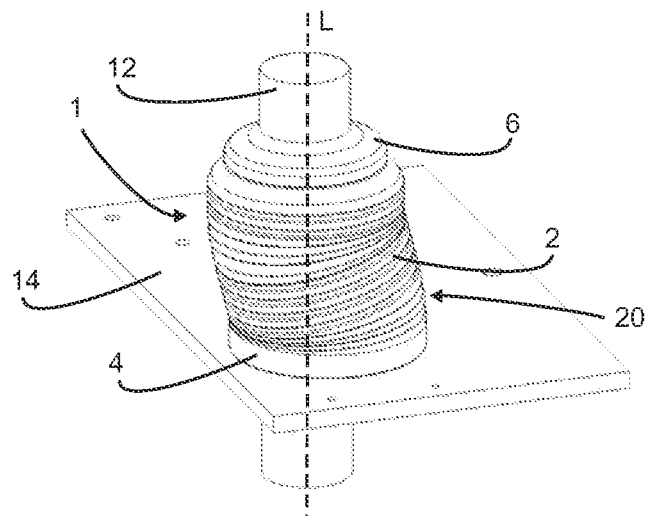
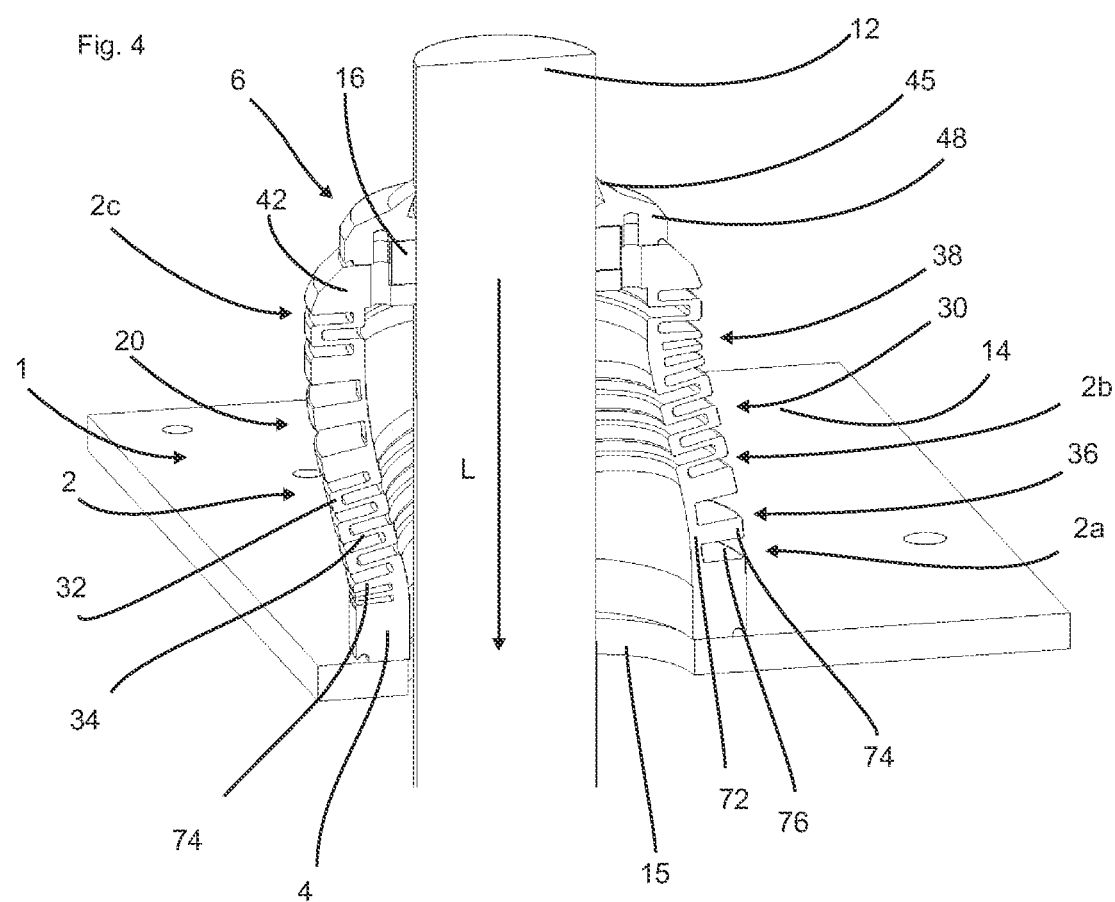

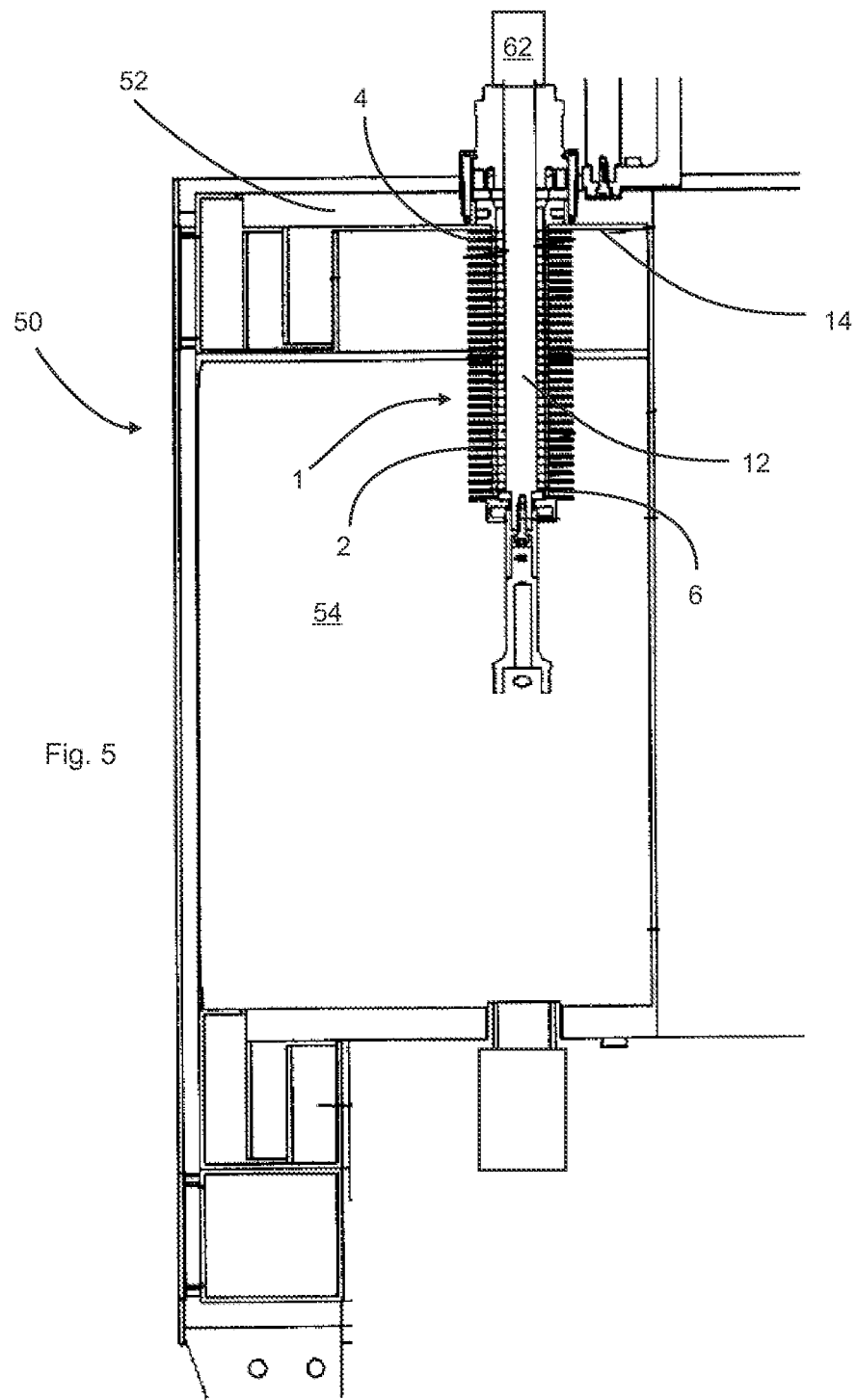

SEAL DEVICE WITH COMPENSATION CAPACITY FOR A PLURALITY OF MOVEMENT DIRECTIONS

BACKGROUND

The present invention relates to the field of the beverage producing industry and to the packaging industry in general. Various apparatuses and methods, which treat containers, such as for example filling devices, closure devices, conveying devices, sterilization devices and the like, are known from the prior art.

In filling certain beverages an attempt is made to carry this out in a sterile room. In these cases the containers are conveyed through a sterile room and are treated, for example filled, closed or sterilized, during this conveying. In this case an attempt is made to ensure as reliable as possible a sealing of this sterile room off from the environment thereof.

Many of the aforesaid treatment devices have treatment elements which perform movements in the interior of the sterile room, such as for example closure heads which screw the closures onto the containers. In addition, an attempt is made to arrange drive devices, such as for example motors but also guide cams, wherever possible outside the sterile room in order to minimize the risk of contamination in this way.

In order nevertheless to provide a capacity of movement for the treatment element arranged in the interior of the sterile room, so-called folding bellows are used in part in the prior art. These folding bellows are arranged in this case both on a portion of the movable element and for example on a portion of a housing wall and, in this way, they seal off the region between the treatment element and the aforesaid wall, so that the folding bellows itself usually also forms a boundary of the clean room. A drawback of bellows of this type lies in the frequently only very restricted capacity of movement. In this way, for example, folding bellows are known which permit a movement in a longitudinal direction of the treatment element and also those which allow a movement in a preferred direction transversely to this direction. In addition, in the case of some treatment elements, however, a rotational movement of the treatment element would also be desirable. Conventional folding bellows are usually not suitable for compensating rotational movements of this type.

SUMMARY

The object of the present invention is therefore to produce a seal device, in particular for beverage plants or container treatment plants, which also allows compensation of rotational movements. This object is attained according to the invention by a seal device as well as an apparatus for the treatment of containers in accordance with the independent claims. Advantageous embodiments and further developments form the subject matter of the sub-claims.

A seal device according to the invention for sealing off intermediate spaces formed between bodies arranged so as to be movable with respect to each other (i.e. in particular bodies movable in a relative manner with respect to each other) has a main body which is formed from a resilient and gas-tight material and which extends completely in a peripheral direction and through which a portion of the first of the two movable bodies is capable of being guided. In addition, the seal device has a first end portion, which is capable of being fastened to the second movable body, and a second end portion, which is capable of being set against the aforesaid first movable body. In addition, the second end portion is movable with respect to the first end portion in a first transverse direction which extends at an angle different from 0° with respect to the longitudinal direction, preferably extends at an angle of at least 60° with respect to the longitudinal direction and is preferably substantially at a right angle to the longitudinal direction. It is preferable for the second end portion to be movable with respect to the first end portion in a second transverse direction which extends at an angle different from 0° with respect to the longitudinal direction and to the first transverse direction and is preferably at a right angle.

According to the invention a sliding seal device, which is capable of being applied to the first body in such a way that a relative rotation is made possible between the first body and the second body by a pre-set angle of rotation, is arranged on the second end portion of the seal device.

A combination of a folding bellows with a sliding seal is thus proposed according to the invention. This seal device affords the advantage that the first movable body is movable in particular in any spatial direction and, in addition, is also rotatable by a pre-set angle with respect to the second body. This rotatability is provided in particular in this case by the sliding seal mentioned above. In this way, a seal is made possible whilst retaining the complete movability of the movable body. In this way, the seal device is suitable for widely varying movement elements, such as occur in the field of the beverage and/or packaging industry. The seal device can thus be used for example as a seal device for a closure head for the closure of containers, and also, on the other hand, for elements such as for example rotatable spray nozzles and the like. This seal device or component parts thereof respectively can be formed from a flexible material, but this is not absolutely necessary. It is preferred for at least one component part of the seal device to be produced from a polymer, and in particular from PTFE. In this way, in particular, annular sealing elements can be produced from PTFE.

It is preferable for a (sealed) rotation to be made possible between the first body and the second body by an angle of rotation which amounts to at least 10°, preferably at least 20°, preferably at least 30 and preferably at least 40°. In the case of a preferred design the movement in the first transverse direction is a pivoting movement of one of the two movable bodies and preferably of the first movable body about a pre-set pivot axis. This means that it is preferable for a distance between the first end portion and the second end portion of the seal device to remain substantially constant during this movement. It is preferable for the first body to be substantially freely rotatable with respect to at least one portion of the seal device. It is preferable for the sliding seal device also to have a rotationally fixed part and a part rotatable with respect to this rotationally fixed part. It is preferable for the seal device to be formed from a folding bellows and a sliding seal device arranged on the latter.

In addition, the sliding seal device can also, however, permit a movement in the longitudinal direction of the first body between the first body and the second body, in particular therefore a movement in which a distance between the end portions of the seal device varies.

In the case of an advantageous embodiment, the main body has portions formed in a different manner in the longitudinal direction thereof. In this case it is possible, in particular, for a first portion of the main body to be inserted in the longitudinal direction in order to compensate longitudinal movements and for another portion to be inserted in order to compensate transverse or pivoting movements respectively. It is advantageous, however, for the individual portions of the main body to be made unchanging in a peripheral direction of the main body. This allows a simplified production of the seal device.

In the case of a further advantageous embodiment, a portion of the main body has a continuous wall preferably meandering (or extending in a zigzag pattern). It is advantageous in this case for the meandering wall to be formed with different wall thicknesses. In this case, these different wall thicknesses can advantageously alternate (in particular periodically). In this way, it is possible for example for those portions of the wall which extend in the longitudinal direction of the main body to have a greater wall thickness than those wall portions which extend in a direction extending at a right angle thereto or in a radial direction of the main body respectively. It is advantageous for the aforesaid wall portions with the greater and the lesser thicknesses to be made at right angles to one another in each case. In this case, it is possible for those wall portions which extend in the radial direction to be used, in particular, for absorbing movements of the moved body in the longitudinal direction specified above.

In the case of a further advantageous embodiment, a portion of the main body has a continuous cylindrical wall on which, in particular, annular projections are formed.

In the case of a further advantageous embodiment, the seal device is produced from a flexible material. It is advantageous for the seal device to be produced from a material which is selected from a group of materials which contains thermoplastic materials, elastomers or metals or combinations of them. These materials are possible both for the sliding seal or the shaft seal ring respectively and for further component parts of the seal device such as for example a folding bellows. In the case of a further advantageous design, the seal device is designed in a plurality of parts. In this way, for example, a shaft seal ring, which forms a component part of the seal device, can be produced from a relatively wear-resistant material, in which case fibre-reinforced thermoplastic materials or PTFE inter alia are possible, which preferably have a proportion of glass fibres of between 5% and 50%, preferably between 10% and 30%.

In the case of a further advantageous embodiment the sliding seal device has a shaft seal ring. It is preferable for this shaft seal ring to co-operate with a sealing lip in order to achieve the sealing effect in the case of rotational movements as well. This means that in this case the movable body is movable in a rotational manner with respect to the seal device. In this way, however, any rotational movements, i.e. also complete rotations or rotations going beyond them, can be performed.

In the case of a further advantageous design the seal device is designed in the form of a folding bellows, whilst a receiving flange is preferably provided at one end or respectively at one end portion. On this side the seal device is fastened to a component to be sealed, such as for example a clean room housing. It is advantageous for the shaft seal ring specified above to be arranged on the other end portion. In this case, the entire component or the seal device respectively can be designed in one piece or can comprise a plurality of parts.

In this way, it is advantageous for the main body of the seal device to be designed at least locally in the form of a folding bellows. In this case, this design in the form of a folding bellows serves, in particular, to compensate longitudinal movements.

In the case of a further advantageous design the seal device is formed in one piece. In this way, it is possible for the seal device to consist of a single material.

It would also be possible, however, for the main body and the sliding seal to be components which are separate but connected to each other. In this way, it would be possible for two or more materials to be joined to one another. It is advantageous for the materials to be joined to one another by material bonding, i.e. for example by sintering.

In addition, it would be possible, however, in the case of a multiple-part design, for the main body and the shaft seal ring to be separate components which are connected to each other, for example which are screwed to each other. This design affords advantages in that overlaid movements, i.e. rotational and pivoting movements and in addition a translational movement, can also be sealed off in a reliable manner.

In the case of a further advantageous embodiment, a continuous projection, on which at least one portion of the sliding seal is arranged, is arranged on the first movable body. In general, it is advantageous for the seal device or the second end portion respectively not to be essentially longitudinally displaceable with respect to the movable component. In other words, although a rotational movement of the movable element with respect to the seal device is preferably possible, a longitudinal displacement of the movable element with respect to the seal device is not. In this way, it may be the case that the aforesaid continuous projection is received by the second end portion of the seal device. It would also be possible, however, for a continuous groove into which a portion of the seal device engages to be formed on the movable body.

In the case of a further advantageous embodiment, the seal device has a groove, which is continuous at least in part and which also extends at least in a radial direction (i.e. optionally also obliquely with respect to the radial direction), for receiving a portion of the first body. It is preferred for this groove to be made continuous in a peripheral direction of the seal device and it preferably has a circular cross-section.

In the case of a further advantageous design, the first end portion is connected in a gas-tight manner to the second body and/or the second end portion is connected in a gas-tight manner to the first movable body. In this case it is preferable for the interfaces also to be designed in a gas-tight manner in the case of a multiple-part design of the seal device.

The present invention further relates to an apparatus for the treatment of containers, which has a conveying device which conveys the containers to be treated along a pre-set conveying path. In addition, the apparatus has a clean room, inside which the containers are conveyed, this clean room being partitioned off from an environment by means of at least one wall. In addition, a treatment element is provided which is movable with respect to the wall and which treats the containers in a pre-set manner, in which case a drive for moving this treatment element is arranged at least locally outside the clean room and the treatment element projects at least locally into the clean room.

In addition, a seal device is provided for sealing off an intermediate space formed between the treatment element and the wall of the clean room, and it has a main body which is formed from a resilient and gas-tight material and which extends about at least one portion of the treatment element completely in a peripheral direction and through which this aforesaid portion of the treatment element is guided.

In addition, the seal device has a first end portion, which is fastened to the wall (advantageously in a gas-tight and liquid-tight manner), and a second end portion, which is applied to the treatment element. In this case, the second end portion is movable with respect to the first end portion.

According to the invention, the second end portion of the seal device has arranged on it a sealing element which is capable of being applied to the treatment element in such a way that a relative rotation between the treatment element and the wall by a pre-set angle of rotation is made possible. It is therefore advantageous for a sliding seal device to be provided as the sealing element.

Within the scope of the present invention, it is therefore proposed that a sealing element of the type described above should be used in particular for apparatuses for the treatment of containers. In this case the first body mentioned above is thus the treatment element and the second body is the wall. In this way, it is preferable for the seal device also to form a boundary of the clean room.

It is advantageous for the second end portion to be movable with respect to the first end portion in a first transverse direction which is at a right angle to the longitudinal direction, and it is advantageous for the second end portion also to be movable with respect to the first end portion in a second transverse direction which is at a right angle to the longitudinal direction and to the first transverse direction.

In this way, as already described above, it is also proposed that one end portion should be movable with respect to the other one essentially in any spatial direction and, in addition, the aforesaid portion of the treatment element is also rotatable with respect to the seal element.

It is advantageous for the apparatus for the treatment of containers to be selected from a group of apparatuses which contains filling devices for the filling of containers, sterilization devices for the sterilization of containers, closure devices for the closing of containers, labelling devices and the like. In addition, the apparatus for the treatment of containers can also be a shaping device for the shaping of plastics material pre-forms into plastics material containers or even a heating device for the heating of plastics material containers.

The drive is advantageously an electric motor drive. It would also be possible, however, for a guide cam (in particular arranged in a stationary manner) to be provided in this case as the moving device, at least for some of the movements, such as for example a reciprocating movement.

It is advantageous for the clean room to have a stationary wall and a wall which is movable with respect to this stationary wall. It is advantageous for the movable wall to be rotatable about a pre-set axis of rotation. In addition, the treatment element can also be arranged on a rotatable carrier.

It is advantageous for the aforesaid stationary and movable walls of the clean room to be sealed off with respect to each other, for example by the use of at least one continuous sealing device which has a channel filled with a liquid. Sealing devices of this type are known as so-called surge chambers from the prior art.

In the case of a further advantageous embodiment the treatment element is selected from a group of treatment elements which contains closure elements for the closing of containers with closures, filling elements for the filling of containers, sterilization elements for the sterilization of containers, holding elements for the holding of containers and the like.

BRIEF DESCRIPTION OF THE DRAWINGS

Further advantages and embodiments are evident from the accompanying drawings. In the drawings

FIG. 3 is an illustration of a seal device according to the invention in a pre-set state of movement;

FIG. 4 is a sectional illustration of the seal device shown in FIG. 3, and

FIG. 5 is an illustration of a treatment device with a seal device according to the invention.

DETAILED DESCRIPTION

Figure 1:
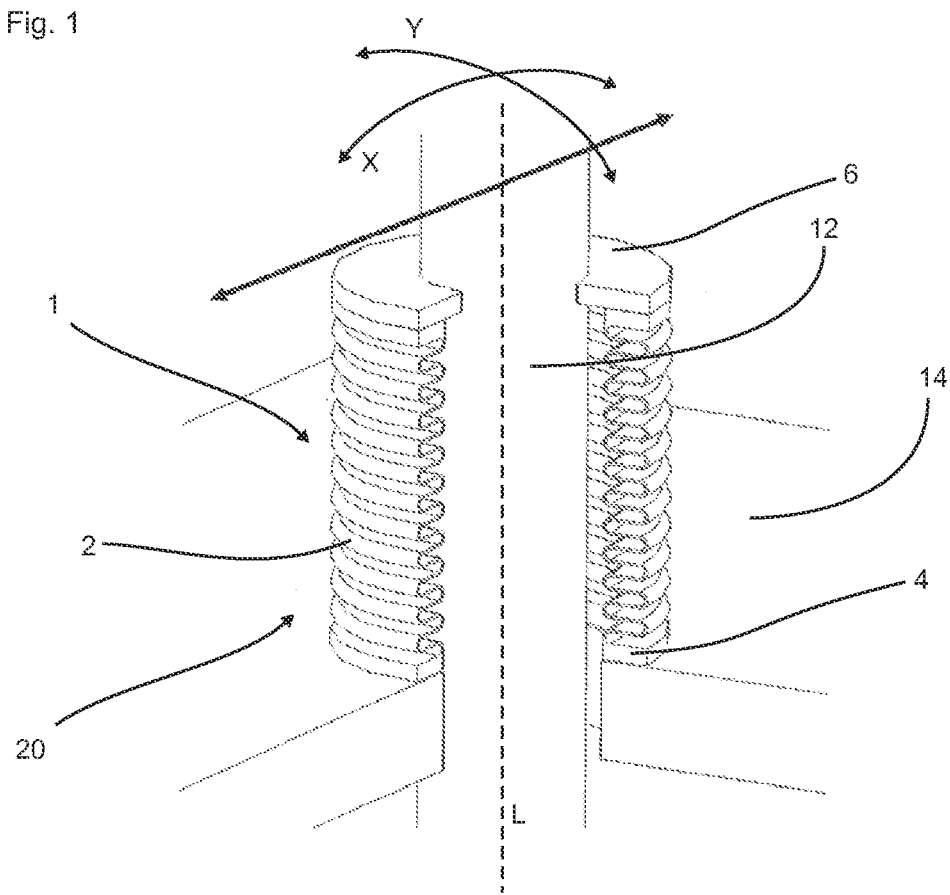
FIG. 1 is a diagrammatic illustration of a seal device.

FIG. 1 shows a seal device 1 in a first highly diagrammatic illustration. In this case a wall 14 or a wall element 14 respectively is provided, as well as a moving element 12 movable with respect to this wall 14, in which case the intermediate space between the wall and the moving element 12 should be sealed off by the seal device 1. In this way it is possible for example for a clean room to be present below the wall 14 and for a (non-sterile) environment to be present above the wall. It is advantageous for the wall 14 to have an opening 15 (see FIG. 2) which has a larger cross-section than the moving element and through which the moving element is guided.

The seal device 1 has a first end portion 4 which is preferably arranged on the wall 14 in a fixed manner. A second end portion 6 of the seal device rests against the moving element 12 which has a bar-like portion here. The reference letter X designates a possible movement direction of the moving element 12. In this case it is possible for the moving element 12 to be moved as a whole, but it would also be possible for the moving element 12 to be pivoted in the direction X. The reference number 2 designates a main body of the seal device 1. In this way, during this pivoting movement the second end portion of the seal device 20 preferably moves along a circular path with respect to the first end portion of the seal device. In addition, it would be possible for the moving element also to be movable in a second direction Y which in this case is at a right angle to the first direction. This could likewise be a pivoting movement. In the case of this design it is preferable for the second end portion 6 to be movable in a spherical plane or respectively area with respect to the first end portion 4.

Figure 2:
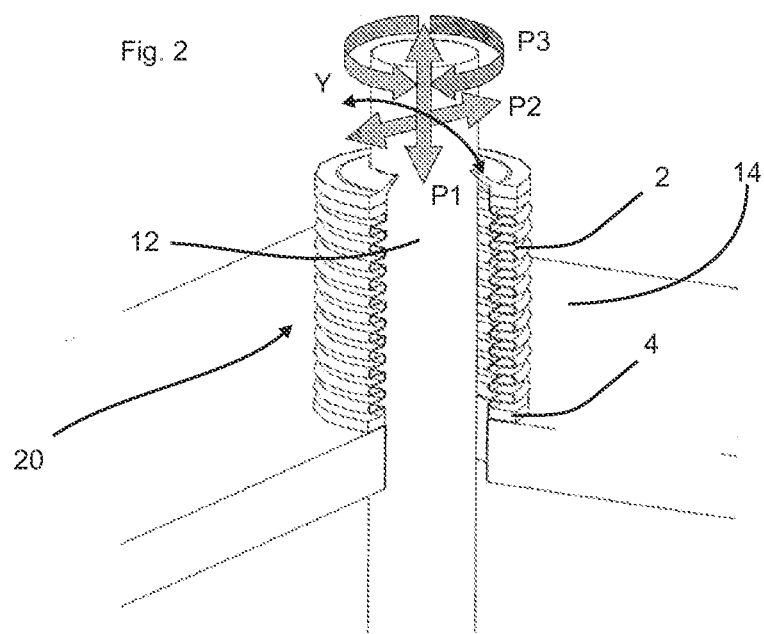
FIG. 2 is an illustration of the seal device whilst taking into consideration the possible movements.

FIG. 2 is an illustration similar to the illustration reproduced in FIG. 1, in which the possible movement directions of the moving element 12 are additionally shown here. It is evident that the moving element 12 can move both in the direction P1, i.e. in the longitudinal direction L of the moving element 12 shown in FIG. 1, and in the direction P2 and also in a direction P4 (not shown here) which is also at a right angle to the directions P1 and P2. Here again a movement capacity in the directions X and Y already shown in FIG. 1, which extend in a straight line or in a circular path respectively, is also possible.

The reference P3 designates a possible rotational movement of the moving element 12. A closure head for the closing of containers could be arranged for example on the moving element. In addition, a drive device which moves the moving element 12 could be provided outside a clean room, i.e. above the wall 14.

FIG. 3 is a perspective illustration of a seal device according to the invention which is arranged on a wall 14. It is evident that in this case the main body 2 is designed in the form of a folding bellows and the first end portion 4 is arranged on the wall 14. In this case the end portion 4 can be designed in the form of an attachment flange which is glued for example to the wall 14. The reference number 20 designates a sliding seal device which is capable of being applied to the moving element 12 or an external surface of the moving element 12 respectively.

The second end portion 6 is preferably designed in this case in the form of a shaft seal ring which allows a relative rotation of the moving element 12 with respect to the main body 2. It is evident that the main body 2 can be twisted in the manner of a concertina, in order to allow the movements of the moving element 12 in particular in the plane of the wall 14 in this way.

FIG. 4 is a sectional illustration of the apparatus shown in FIG. 3. The first end portion 4, which is arranged on the wall 14, is again evident here. In this case, as mentioned above, the second end portion 6 of the seal device 1 rests in part against the moving element 12. For this purpose a continuous projection or collar 16 respectively can be formed on the moving element 12. This continuous collar 16 engages in the one recess formed in the second end portion 6. For this purpose the second end portion 6 can have a first receiving element 42, as well as a second receiving element 48 capable of being screwed for example to this first receiving element 42, it being possible for the continuous projection 16 to be inserted between these two receiving elements 42 and 48. The reference number 45 designates a sealing lip which can rest against the moving element 12. In this way, a seal—for example a sliding seal (for example through a shaft seal), which also allows a relative rotation of the moving element 12—is made possible between the moving element 12 and the second end portion 6.

In addition, it is evident that in this case the main body 2 has different designs. In a lower region 2a the main body has a continuous wall 72 as well as annular projections 74 which extend radially outwards in this case. Corresponding projections which extend radially inwards would also be possible.

This portion 2a serves in particular in this case to absorb transverse movements, i.e. movements which extend in the plane of the wall 14. Grooves 76 are formed in each case between these annular projections 74.

The reference 2b designates a further portion of the main body which in this case is designed in the form of a wall of zigzag shape. This wall has in this case portions 32 which extend at a right angle, i.e. in the longitudinal direction L, in a non-stressed state of the moving element, i.e. in a state in which the latter is in a middle setting with respect to the wall. In addition, second wall portions 34 are provided which extend in this case in a radial direction with respect to the longitudinal direction L. In particular, these portions 34 serve in this case to absorb or respectively compensate movements of the moving element 12 in the longitudinal direction L thereof, i.e. in particular for reciprocating movements.

A third portion 2c of the main body is again designed like the first portion 2a and, as shown in FIG. 4, again serves to absorb transverse movements. In this way, an S-shaped deformation of the seal device 2 during a transverse movement of the moving element 12 is made possible.

It would also be possible, however, for all the walls of the folding bellows or the seal device respectively to be designed in the same way (preferably both in the longitudinal direction L and in the peripheral direction extending around the longitudinal direction). An embodiment of this type is also preferred.

FIG. 5 is a diagrammatic illustration of an apparatus for the treatment of containers, in which the seal device shown in the figures specified above is used. The roughly diagrammatic illustration reproduced in FIG. 5 is not a specific apparatus 50, but this illustration serves only to explain the invention. The apparatus has a treatment element 12 which is designed in the form of a rod and which extends through a wall 14 into a clean room 54. A holding element which holds a container (not shown) can be arranged at the lower end of the treatment element 12, but an actuating element would also be possible which is suitable for initiating a specified procedure, such as for example a locking or an unlocking procedure of blow moulds or mould carriers or respectively blow mould stations in a stretch blow moulding machine. The above-mentioned movements in the X or Y direction are not shown in FIG. 5.

It is preferable for the apparatus 50 to be an apparatus for shaping plastics material pre-forms into plastics material containers, such as in particular a stretch blow moulding machine. The containers to be treated are, in particular, plastics material pre-forms or plastic bottles. The treatment element 12 corresponds in this case to the above-mentioned first body and the wall 14 to the above-mentioned second body.

The reference number 52 designates a conveying device which serves, in particular, to convey the containers to be treated. In this case this conveying device can be a carrier wheel, in particular, a blow moulding wheel on which a plurality of treatment devices for the treatment of plastics material containers are arranged. It is preferable in this case for each of these treatment units to have a treatment element 12.

The reference number 1 designates a seal device. A first end portion 4 is arranged in this case on the wall 14 and the treatment element 12 is capable of being applied to a second end portion 6 in such a way that it is rotatable about its longitudinal axis. The reference number 62 designates a drive or a drive device respectively for driving the treatment element 12, which drive device is arranged outside the clean room 54. Not shown in this figure is the pivotability of the treatment element 12 made possible by the seal device according to the invention. This treatment element could be pivotable for example about an axis which extends at a right angle to the treatment element in the plane of the wall. The reference number 2 again designates the main body of the seal device 1 in the manner of a folding bellows.

The invention claimed is:

1. A seal device for sealing off intermediate spaces formed between bodies arranged so as to be movable with respect to each other, comprising: a main body formed from a resilient and gas-tight material and which extends completely in a peripheral direction and through which a portion of the first of the two bodies is capable of being guided, and a first end portion, which is fastened to the second body, and a second end portion, which is set against the first movable body, wherein the second end portion is movable with respect to the first end portion in a first transverse direction which extends at an angle different from 0° with respect to a longitudinal direction, wherein a sliding seal device, which is applied to the first movable body in such a way that a relative rotation is made possible between the first body and the second body by a pre-set angle, is arranged on the second end portion of the seal device.

2. The seal device according to claim 1, wherein the sliding seal device has a shaft seal ring.

3. The seal device according to claim 1, wherein the first transverse direction is substantially at a right angle to the longitudinal direction.

4. The seal device according to claim 1, wherein the main body is designed at least locally in the form of a folding bellows.

5. The seal device according to claim 1, wherein a receiving flange is provided on the first end portion.

6. The seal device according to claim 1, wherein the seal device is formed in one piece.

7. The seal device according to claim 1, wherein the main body and the sliding seal are elements which are separately connected to each other.

8. The seal device according to claim 1, wherein a continuous projection, on which at least one portion of the sliding seal is arranged, is arranged on the first movable body.

9. The seal device according to claim 1, wherein the second end portion is movable with respect to the first end portion in a second transverse direction which extends at an angle different from 0° with respect to the longitudinal direction and to the first transverse direction.

10. The seal device according to claim 1, wherein the first end portion is connected in a gas-tight manner to the second body and/or the second end portion is connected in a gas-tight manner to the first movable body.

11. The seal device according to claim 1, wherein a rotation between the first body and the second body is made by an angle of rotation of at least 10°.

12. The seal device according to claim 1, wherein the movement of the first transverse direction (X) is a pivoting movement of one of the two movable bodies.

13. The seal device according to claim 12, wherein the movement of the first transverse direction (X) is a pivoting movement of the first movable body about a pre-set pivot axis.

14. The seal device according to claim 1, wherein a portion of the main body has a continuous meandering wall.

15. The seal device according to claim 14, wherein the meandering wall is formed with different, alternating wall thicknesses.

16. The seal device according to claim 1, wherein the seal device has a groove that is continuous in a peripheral direction of the seal device and has a circular cross-section.

17. An apparatus for the treatment of containers, comprising: a conveying device which conveys the containers to be treated along a pre-set conveying path; a clean room, inside which the containers are conveyed, wherein this clean room is partitioned off from an environment by means of at least one wall; a treatment element which is movable with respect to the wall and which treats the containers in a pre-set manner; a drive for moving this treatment element is arranged at least locally outside the clean room and the treatment element projects at least locally into the clean room; and with a seal device for sealing off an intermediate space formed between the treatment element and the wall of the clean room; wherein the seal device has a main body which is formed from a resilient and gas-tight material and which extends completely in a peripheral direction and through which a portion of the treatment element is guided; as well as a first end portion, which is fastened to the wall, and a second end portion, which is capable of being applied to the treatment element; wherein the second end portion of the seal device has arranged on it a sealing element which is capable of being applied to the treatment element in such a way that a relative rotation between the first body and the second body by a pre-set angle of rotation is made possible.

18. The apparatus according to claim 17, wherein the second end portion is movable with respect to the first end portion in a first transverse direction which is substantially at a right angle to the longitudinal direction.

19. The apparatus according to claim 17, wherein the treatment element is selected from a group of treatment elements which contains closure elements for the closing of containers with closures, filling elements for the filling of containers, sterilization elements for the sterilization of containers, holding elements for the holding of containers and the like.

* * * * *